(12) United States Patent
Matthiesen et al.

(10) Patent No.: US 10,568,534 B2
(45) Date of Patent: Feb. 25, 2020

(54) SYSTEM AND METHOD FOR PROCESSING SIGNALS FROM INTRACARDIAC CATHETERS

(71) Applicant: CathVision ApS, København N (DK)

(72) Inventors: Mads Emil Matthiesen, Copenhagen V (DK); Sigge Nejst Larsen, Copenhagen N (DK)

(73) Assignee: Cath Vision ApS, København N (DK)

( * ) Notice: Subject to any disclaimer, the term of this patent is extended or adjusted under 35 U.S.C. 154(b) by 114 days.

(21) Appl. No.: 15/564,670

(22) PCT Filed: Apr. 8, 2016

(86) PCT No.: PCT/EP2016/057783
§ 371 (c)(1),
(2) Date: Oct. 5, 2017

(87) PCT Pub. No.: WO2016/162497
PCT Pub. Date: Oct. 13, 2016

(65) Prior Publication Data
US 2018/0092563 A1    Apr. 5, 2018

(30) Foreign Application Priority Data
Apr. 10, 2015   (EP) ..................... 15163168

(51) Int. Cl.
*A61B 5/0428* (2006.01)
*A61B 5/00* (2006.01)
(Continued)

(52) U.S. Cl.
CPC .......... *A61B 5/0428* (2013.01); *A61B 5/6852* (2013.01); *A61B 5/7203* (2013.01); *A61B 5/0476* (2013.01); *A61N 1/368* (2013.01)

(58) Field of Classification Search
CPC ... A61B 5/0428; A61B 5/6852; A61B 5/7203; A61B 5/0476; A61N 1/368
(Continued)

(56) References Cited

U.S. PATENT DOCUMENTS

2005/0119708 A1   6/2005  Haefner
2006/0293603 A1*  12/2006 Strandberg ........... A61B 5/0422
                                                          600/509
(Continued)

FOREIGN PATENT DOCUMENTS

CA      2359445 A1    4/2003
EP      2446814 A1    5/2012
(Continued)

OTHER PUBLICATIONS

International Search Report corresponding to International Patent Application No. PCT/EP2016/057783, European Patent Office, dated Jun. 17, 2016; (4 pages).
(Continued)

Primary Examiner — Amanda K Hulbert
Assistant Examiner — Philip C Edwards
(74) Attorney, Agent, or Firm — Nixon Peabody LLP (57) ABSTRACT

A system for recording intracardiac signals and for providing stimulation pulses and/or ablation energy at intracardiac locations. The system includes intracardiac terminals adapted to collecting intracardiac electrophysiological potentials from respective intracardiac locations in an individual; an indifferent terminal adapted to collecting indifferent electro-physiological potentials from the individual; a differential amplifier stage adapted to receiving and amplifying the electrophysiological potentials collected from the intra-cardiac and indifferent terminals with respect to a signal reference to obtain respective intracardiac and indifferent signals; a processor device adapted to determining a
(Continued)

common mode signal as an average of the intracardiac and indifferent signals and adapted to providing an output of intracardiac data based at least on the intracardiac signals, wherein the intracardiac signals are referenced with respect to the common mode signal. A method of processing intracardiac electrophysiological signals is also disclosed.

20 Claims, 6 Drawing Sheets

(51) Int. Cl.
 *A61B 5/0476* (2006.01)
 *A61N 1/368* (2006.01)
(58) Field of Classification Search
 USPC .......................................................... 600/509
 See application file for complete search history.

(56) References Cited

U.S. PATENT DOCUMENTS

| 2011/0190625 | A1 | 8/2011 | Harley et al. |
| 2011/0227638 | A1 | 9/2011 | Peuscher |
| 2013/0184600 | A1 | 6/2013 | Tan et al. |
| 2014/0121548 | A1 | 5/2014 | Lou et al. |
| 2015/0005585 | A1* | 1/2015 | Xu ........................ A61B 5/0402 600/300 |
| 2016/0166171 | A1 | 6/2016 | Warner et al. |

FOREIGN PATENT DOCUMENTS

| EP | 2740403 A1 | 6/2014 |
| JP | 2011072725 | 4/2011 |
| WO | 2010/103542 A1 | 9/2010 |

OTHER PUBLICATIONS

International Written Opinion corresponding to International Patent Application No. PCT/EP2016/057783, European Patent Office, dated Jun. 17, 2016; (6 pages).

William G Stevenson et al.—"Recording Techniques for Clinical Electrophysiology"—Journal of Cardiovascular Electrophysiology; Dated Sep. 2005 (6 pages).

Razzaq Nauman et al: An intelligent adaptive filter for elimination of power line interference from high resolution electrocardiogram, IEEE Access, vol. 4, 31, Dated Mar. 2016 (13 pages).

Yegui Xiao et al: A new LMS-based Fourier analyzer in the presence of frequency mismarh and applications; IEEE Transactions on circuit and systems part I: Regular papers, vol. 52, No. 1, 1 Dated Jan. 2005 (16 pages).

\* cited by examiner

SYSTEM AND METHOD FOR PROCESSING SIGNALS FROM INTRACARDIAC CATHETERS

CROSS-REFERENCE TO RELATED APPLICATIONS

This application is a U.S. National Stage of International Application No. PCT/EP2016/057783, filed Apr. 8, 2016, which claims the benefit of European Patent Application No. 15163168.6, filed Apr. 10, 2015, both of which are incorporated herein by reference in their entireties.

The present invention relates in one aspect to a system for recording intracardiac signals, and in particular to a system for recording intracardiac signals representing electrophysiological potentials from a plurality of electrodes at respective intracardiac locations. In a further aspect, the invention relates to a method for processing intracardiac signals, in particular a method for processing intracardiac signals representing electrophysiological potentials probed by a plurality of electrodes at respective intracardiac locations. In yet a further aspect, the present invention relates to a system for performing intracardiac procedures including steps of recording intracardiac signals and steps of applying stimulus and/or ablation energy at intracardiac locations.

BACKGROUND OF THE INVENTION

Intracardiac electrophysiological measurements are considered an important tool for understanding and treating cardiac problems, such as arrhythmia phenomena. Intracardiac measurements are obtained in so-called minimally invasive procedures using intracardiac catheters. Advanced equipment includes multiple electrode catheters having a plurality of electrodes that can be located inside the heart. Depending on the procedures to be performed, such catheters are at their distal end equipped with electrodes configured for picking up an electrophysiological potential at the respective location of the electrodes. The electrophysiological potentials are passed via electrical conductors from the distal end of the catheter to a connector interface at the proximal end of the catheter, and further to recording equipment for amplification, processing, display and storage of signals representative of the intracardiac electrophysiological potentials. The intracardiac electrophysiological signals are the observation of the intracardiac electrophysiological potentials as a function of time, wherein the intracardiac electrophysiological signals are measured by amplifying the potential difference between a first terminal and a second terminal, wherein at least the first terminal is connected to an electrode that is placed inside the heart. The obtained intracardiac signals may be further amplified/processed and/or digitized for display on a computer and/or storage on a digital storage medium.

By recording/mapping a plurality of electrophysiological signals from signal electrodes placed inside the heart, details about a pathological state relating to cardiac arrhythmia in an individual can be obtained and proper treatment, such as an ablation treatment, can be developed. The aspects of the recorded intracardiac signals to be studied include the presence or absence of characteristic features in a given signal, the periodicity and regularity of repetition of the signals, as well as the amplitude and morphology of the signals.

A major challenge in the recording of intracardiac electrophysiological signals is the interference from electrical noise sources, which is picked up by the highly sensitive apparatus. Amongst the main causes for such noise is in particular the prominent mains interference at around 50 Hz or around 60 Hz—depending on the local frequency standard for mains supply. Other sources of noise include internal amplifier noise, artefacts due to movement of the wiring used for recording, and electrode DC-offsets. The noise may include noise components common to all signals (common mode noise) and noise components that vary from signal to signal (differential mode noise).

Processing the signals e.g. by filtering at frequencies corresponding to the noise sources may suppress some of the noise. However such filtering tends to affect the morphology of the signals and therefore has to be done with the utmost care.

US 2015/0005585 A1 discloses a system and method for the acquisition of bio-potential signals, such as, for example, ECG (electrocardiography), EEG (electroencephalography), or EMG (electromyography) signals. The disclosed biopotential acquisition system uses multiple active electrodes attached to the outside of the body, in which each of the electrodes is integrated with an amplifier and an analogue-to-digital converter for the suppression of interference picked up from cables. An improvement of the bio-potential acquisition system according to US 2015/0005585 A1, resides in adjusting the gain of the amplifiers to compensate for component mismatch by feeding back a common mode test signal to an adjustable gain control of the amplifiers in the respective active electrodes. However, the system of US 2015/0005585 A1 relies on the use of active electrodes, in which pre-amplifying electronics is located next to and integrated with a passive electrode. The use of such active electrodes is incompatible with the particularly stringent spatial constraints for acquiring potentials from intracardiac locations—or would at least lead to a prohibitively complex design of the instruments/catheters for minimally invasive procedures, in particular when multiple electrodes are to be placed in intracardiac locations. Furthermore, the use of pre-amplifying electronics next to an electrode in an intracardiac location is incompatible with the desire to not only record signals when performing intracardiac procedures, but also to pass a stimulus pulse or even ablation energy there through.

Two configurations for measuring intracardiac electrophysiological signals are known—a unipolar configuration and a bipolar configuration. In the unipolar configuration, the intracardiac signal is recorded by referencing the electrophysiological potentials from the intracardiac signal electrode to a so-called indifferent electrode, which is considered to provide a potential reference that is largely independent of the local potential inside the heart. The indifferent electrode is typically arranged outside and distant from the heart. Commonly, the indifferent reference is obtained from electrodes arranged on the outside surface of the individual, such as a Wilson central terminal (WCT) defined by connecting electrodes arranged on the arms and the left leg of a patient through high impedance resistors. However, recent studies also suggest using an intravascular electrode as reference electrode in order to reduce pick-up of electro-magnetic interference. Such an intravascular electrode is, for example, advantageously arranged in the inferior vena cava (Stevenson et al., Journal of Cardiovascular Electrophysiology, 2005, pp. 1017-1022). Advantages of unipolar recordings include providing an increased spatial resolution of the local potentials at the signal electrode, providing information about the direction of impulse propagation, and allowing to pace and record at the same location. Disadvantages of unipolar recordings include a strong susceptibility to mains interference, and a tendency to retain far-field components that make it difficult to separate local from distant activity in the recorded signal. In the bipolar configuration the intracardiac signal is recorded as the difference between two neighbouring intracardiac electrodes. Thereby, far-field components of the recorded signal are largely eliminated, leaving the local components of the electrophysiological signal. Advantages of the bipolar configuration include a low susceptibility to noise interference, and a more precise capture of high-frequency components. Disadvantages of the bipolar configuration include that the direction of propagation of activation with respect to the orientation of the electrode pair affects the amplitude of the recorded signal. The bipolar signal therefore does not provide reliable information on the direction of propagation of an activation wave front. Furthermore, the spatial resolution of the bipolar configuration is limited by the spatial separation between the two intracardiac electrodes used.

A disadvantage of intracardiac electrophysiological signals obtained from known setups is therefore, that a user of the signals is confronted with data that is excessively noisy or deprived of valuable information content that may be useful, or even indispensable, in the context of a particular study, analysis, diagnosis or treatment for which the data is to be used.

It is therefore desirable to provide a technique for obtaining intracardiac electrophysiological signals that allows for an efficient suppression of noise; that is easily reconfigurable depending on context; that overcomes at least some of the above-mentioned limitations; and/or that provides an alternative to known systems. In addition thereto, it is desirable that such technique further allows for immediately performing intracardiac procedures including steps of recording intracardiac signals and steps of applying intracardiac stimulus and/or ablation energy using the same hardware. This requirement imposes strict constraints on the architecture of the system to ensure compatibility of the hardware with these uses.

SUMMARY OF THE INVENTION

According to a broad aspect of the invention, a system for recording intracardiac signals comprises a plurality of intracardiac terminals adapted to collecting intracardiac electrophysiological potentials from electrodes probing respective intracardiac locations in an individual; amplifying means adapted to amplifying the collected intracardiac electrophysiological potentials with respect to a signal reference to obtain intracardiac signals; a processor device adapted to determining a common mode signal as an average of the intracardiac signals, adapted to determining respective differential mode intracardiac signals by subtracting the common mode signal from the intracardiac signals, and adapted to providing intracardiac data as an output based on the differential mode intracardiac signals.

By separating the common mode signal from the differential mode signals, the overall mains interference is efficiently suppressed. In particular, when using an amplifier stage of the average reference amplifier type in the recording stage for amplifying the collected intracardiac electrophysiological potentials, noise is therefore surprisingly well reduced.

However, the morphology of the differential mode intracardiac signals has changed as compared to traditional type unipolar or bipolar leads. Despite a remarkable noise reduction, differential mode signals may therefore in many practical applications be inexpedient for the subsequent interpretation of the obtained intracardiac data, e.g. with respect to the propagation of an activation signal through a particular electrophysiological region within the heart.

Without being bound by theory, it may further be noted that the signal reference in such a configuration is an average of the intracardiac potentials, which due to its definition as an average is affected by the actual potentials that have been probed by the individual intracardiac electrodes. The signal reference is thus affected by the actual locations of the intracardiac electrodes within the intracardiac region to be studied and may be difficult to relate to a well-defined electrophysiological reference.

According to a preferred aspect, the object of the invention is achieved by a system for recording intracardiac signals, the system comprising a plurality of intracardiac terminals adapted to collecting intracardiac electrophysiological potentials from a plurality of intracardiac electrodes at respective intracardiac locations in an individual;

an indifferent terminal adapted to collecting indifferent electrophysiological potentials from the individual;

a differential amplifier stage adapted to receiving and amplifying the electrophysiological potentials collected from the intracardiac and indifferent terminals with respect to a signal reference to obtain respective intracardiac and indifferent signals;

a processor device adapted to determining a common mode signal as an average of the intracardiac and indifferent signals and adapted to providing an output of intracardiac data based at least on the intracardiac signals, wherein the intracardiac signals are referenced with respect to the common mode signal.

Advantageously according to one embodiment, the system further comprises the plurality of passive intracardiac electrodes adapted for placement at intracardiac locations in the individual. Further advantageously, the system further comprises one or more indifferent electrodes adapted for placement in or on the individual.

Advantageously according to one embodiment, a system for recording intracardiac signals and for providing stimulation pulses and/or ablation energy at intracardiac locations is provided, the system comprising a plurality of passive intracardiac electrodes (1*a-d*) adapted for placement at intracardiac locations in an individual (99);

a plurality of intracardiac terminals (10*a-d*) adapted to collecting respective intracardiac electrophysiological potentials from the plurality of passive intracardiac electrodes (1*a-d*);

one or more indifferent electrodes (2) adapted for placement in or on the individual (99);

an indifferent terminal (20) adapted to collecting indifferent electrophysiological potentials from the one or more indifferent electrodes (2);

a differential amplifier stage (30) adapted to receiving and amplifying the electrophysiological potentials collected from the intracardiac and indifferent terminals (10*a-d*, 20) with respect to a signal reference to obtain respective intracardiac and indifferent signals (201*a-d*, 202); and a processor device 40 adapted to determining a common mode signal (900) as an average of the intracardiac and indifferent signals (201*a-d*, 202) and adapted to providing an output of intracardiac data based at least on the intracardiac signals (201*a-d*), wherein the intracardiac signals (201*a-d*) are referenced with respect to the common mode signal (900).

In operation, the intracardiac terminals collect intracardiac electrophysiological potentials from corresponding intracardiac electrodes placed in the heart of the individual. A plurality of electrodes is provided to simultaneously probe electrophysiological potentials at different locations within an electro-physiologically connected region in a synchronized manner, e.g. for observing the propagation of an activation potential through that region. The electrodes are typically arranged at a distal end of a multiple electrode catheter adapted for intracardiac procedures including measuring/probing, pacing, and/or ablation. The electrodes used for measuring are adapted for probing a potential at an intracardiac location in the individual. An electrical conductor connects the probing electrode to a proximal interface where the probed potential can be collected by a corresponding intracardiac terminal of the recording system. Furthermore, the indifferent terminal collects an indifferent electrophysiological potential from one or more indifferent electrodes placed in or on the individual. The one or more indifferent electrodes probing/defining the indifferent electrophysiological potential have to be located "distant" from the electrophysiological region to be measured/mapped to provide an electrophysiological reference potential that is essentially indifferent with respect to the electrophysiological potentials in the region to be measured/mapped. For ease of access and availability, the indifferent terminal may be collected from electrodes probing body surface potentials, such as a Wilson Central Terminal defining a known electrophysiological reference. Preferably, the indifferent terminal is adapted to collecting electrophysiological potentials from electrodes probing an intra-cardiovascular location, wherein a preferred location for probing a useful signal reference is the inferior vena cava. Other intra-cardiovascular locations are, however, conceivable.

By including an indifferent signal from an indifferent terminal, requiring the indifferent signal to be included in the common mode signal, and referencing the intracardiac signal with respect to that common mode signal, noise reduced intracardiac data is obtained, which is related to a reliable electrophysiological reference. Based on this improved data, output signals with a reliable morphology may be derived.

Most preferably, the processor device is a digital processor device. By performing at least a part of the processing of the signals in a digital processor device a significantly improved flexibility is achieved allowing for tailoring, configuring and reconfiguring the signal recording and processing according to e.g. the context of a specific set-up, the intracardiac procedures to be performed, and/or a particular noise environment.

Further according to one embodiment of the system for recording intracardiac signals, the differential amplifier stage is an average reference amplifier, wherein the average of the intracardiac and indifferent signals is fed back as a signal reference to the input side of the differential amplifier stage so as to reference the intracardiac signals and the indifferent signal to the common mode signal. Thereby, a surprisingly good mains interference suppression is already achieved in the amplifier stage for the intracardiac signals and, where applicable, also for the indifferent signal. The differential amplifier stage thus provides significantly less noisy signals to the processor device for subsequent processing in the digital domain. The average to be fed back may be determined analogue or digital, within the amplifier stage or by the processor device, and suitably converted for being used as a signal reference in the differential amplifier stage. Note, that even though the average of the intracardiac and indifferent signals in this configuration may already be determined within the amplifier stage, the obtained average also corresponds to the common mode signal of the intracardiac and indifferent signals.

According to another embodiment of the system for recording intracardiac signals, the differential amplifier stage is a common reference amplifier, wherein a common reference signal is provided to the channels of the differential amplifier stage for amplifying the intracardiac signals and, where present, the indifferent signal. The common reference signal is preferably defined by one or more electrodes providing a well-defined electrophysiological potential independent of the electrophysiological potentials collected by the intracardiac terminals and, where present, by the indifferent terminal. Preferably, the common reference signal is defined such that it may be considered an electrophysiological reference point or electrophysiological "zero" of the individual.

In general, the signal reference for all channels of the differential amplifier stage is either the same, or the signal references of the different channels are at least unambiguously related to each other. The former is preferable, when the amplifier channels are for signals collected by similar probes. The latter, more complex configuration may be a necessity when some of the probes are subject to particular constraints resulting in differing hardware requirements, such as electrical protection requirements for different channels/terminals for patient safety reasons, for the protection of the apparatus, or for the protection of a user of the apparatus. Such requirements may include defibrillation protection, specific filtering needs for some of the probes, and/or specific bandwidth requirements for intracardiac channels as compared to other channels. In all cases, the intracardiac signals and, where present, the indifferent signal have to be synchronized with respect to each other.

Further according to one embodiment of the system for recording intracardiac signals the processor device is further adapted to determining respective differential mode intracardiac signals by subtracting the common mode signal from the intracardiac signals so as to reference the intracardiac signals to the common mode signal. Thereby, a strict separation of the intracardiac signals into differential mode components and a common mode component is achieved. The differential mode components are indicative of the local variations in the intracardiac signals with a spatial resolution corresponding to the dimension of the probing electrode from which the electrophysiological potential has been collected. The common mode component contains common noise affecting all intracardiac probes and amplifier channels, such as power line interference, but also far field components of the electrophysiological environment probed commonly by all the intracardiac electrodes. A surprisingly efficient suppression of the power line interference is achieved in the differential mode intracardiac signals also for signals obtained using a set-up or an amplifier configuration with less than ideal power line interference suppression. The separation into differential mode signals and a common mode signal thus allows for reducing the noise in intracardiac signals probed by a single electrode to a level that makes it possible to identify localized variations with the spatial resolution of a single electrode.

Further according to one embodiment of the system for recording intracardiac signals the processor device is further adapted to determining a differential mode indifferent signal by subtracting the common mode signal from the indifferent signal. Thereby bringing the indifferent signal in line with the intracardiac signals, wherein the common mode signal is obtained as the average of the intracardiac and indifferent signals.

Further according to one embodiment of the system for recording intracardiac signals, the intracardiac data comprises an ensemble of the differential mode intracardiac signals and/or the differential mode indifferent signal;

an ensemble of unipolar intracardiac signals obtained by subtracting the indifferent signal from the intracardiac signals; and/or an ensemble of unipolar intracardiac signals obtained by subtracting the differential mode indifferent signal from the differential mode intracardiac signals; and/or an ensemble of bipolar intracardiac signals obtained by subtracting a second one of the intracardiac signals from a first one of the intracardiac signals; and/or an ensemble of bipolar intracardiac signals obtained by subtracting a second one of the differential mode intracardiac signals from a first one of the differential mode intracardiac signals.

By including these signals in the intracardiac data, the following advantages are achieved. As mentioned above separation into differential mode signals and a common mode signal allows for reducing the power line noise in intracardiac signals probed by a single electrode to a level that makes it possible to identify localized variations with the spatial resolution of a single electrode. By referring the intracardiac signals to the indifferent signal or equivalently by referring the differential mode intracardiac signals to the differential mode indifferent signal, unipolar intracardiac signals with a well-defined morphology are obtained. Accordingly, also bipolar intracardiac signals may be obtained by referring two intracardiac signals to each other, or equivalently by referring two differential mode intracardiac signals to each other.

Further according to one embodiment of the system for recording intracardiac signals the indifferent terminal is adapted to collecting indifferent electrophysiological potentials from one or more indifferent electrodes probing an intra-cardiovascular location in the individual. By using an indifferent signal that has been collected from an electrode in an intra-cardiovascular location, a closer resemblance of the noise environment seen by the intracardiac probes and the indifferent probe is achieved as compared to other locations, such as a body surface probe, resulting in an improved suppression of the noise components as common mode noise. A particularly advantageous intra-cardiovascular location for probing an indifferent electrophysiological potential is in the inferior vena cava.

According to one embodiment of the system for recording intracardiac signals, the processor device further implements filtering means adapted for selectively filtering the intracardiac and indifferent signals and/or the differential mode intracardiac and indifferent signals, prior to generating intracardiac output data. By implementing the filtering in the processor device, full flexibility for tailoring the filters is achieved, e.g. for the context of a specific set-up, for the characteristics of a specific channel, for the intracardiac procedures to be performed, and/or for a particular noise environment. The selective filtering may include noise frequency tracking filtering or otherwise adaptive filtering, e.g. using noise pattern recognition for estimating the noise pattern from the common mode signal and/or from additional information, such as mains frequency, synchronously monitored mains frequency, or the like. The filter characteristics of the adaptive filter may then be adapted according to that noise pattern and/or additional information.

According to a further aspect of the invention, a measuring system for probing and recording intracardiac signals includes a recording system for recording intracardiac signals according to any of the above-mentioned embodiments, and further includes one or more intracardiac catheters having at a distal end multiple intracardiac electrodes for probing intracardiac electrophysiological potentials, and having at a proximal end an interface for providing the probed intracardiac electrophysiological potentials to the intracardiac terminals of the recording system. More preferably, the measuring system further comprises one or more indifferent electrodes adapted for probing an indifferent electrophysiological potential and connected to an interface for providing the probed indifferent electrophysiological potential to the indifferent terminal of the recording system. Most preferably, the one or more indifferent electrodes are arranged on a catheter for probing the indifferent electrophysiological potential at an intra-cardiovascular location, such as in the inferior vena cava. Advantageously, the intracardiac and indifferent electrodes are arranged on the same catheter.

According to a second preferred aspect, the object of the invention is achieved by a method for processing intracardiac signals as disclosed in the following, wherein the same advantages as discussed above with respect to the system are also achieved by the corresponding features of the method.

According to one embodiment, a method for processing intracardiac signals comprises:

receiving multiple sequences of electrophysiological potentials collected from a plurality of intracardiac terminals and an indifferent terminal;

amplifying the electrophysiological potentials in a differential amplifier stage with respect to a signal reference to obtain respective intracardiac and indifferent signals;

determining a common mode signal as an average of the intracardiac and indifferent signals; and providing an output of intracardiac data based at least on the intracardiac signals, wherein the intracardiac signals are referenced with respect to the common mode signal.

The electrophysiological potentials have preferably been collected from a plurality of intracardiac electrodes at intracardiac locations in an individual via corresponding intracardiac terminals and from at least one indifferent electrode in or on the individual via one or more corresponding indifferent terminals. At least when placed in the individual, the electrodes are most preferably passive electrodes.

Further according to one embodiment of the method for processing intracardiac signals, the method further comprises feeding the average of the intracardiac and indifferent signals back to the input side of the amplifier stage in an average reference amplifier configuration so as to reference the intracardiac signals and the indifferent signal with respect to the common mode signal.

Further according to one embodiment of the method for processing intracardiac signals, the method further comprises subtracting the indifferent signal from one or more of the intracardiac signals to generate respective unipolar intracardiac output signals.

Further according to one embodiment of the method for processing intracardiac signals, the method further comprises selectively applying a channel-specific filtering step to one or more of the intracardiac and indifferent signals prior to generating the intracardiac output signals.

Further according to one embodiment of the method for processing intracardiac signals, the method further comprises subtracting the common mode signal from one or more of the intracardiac signals to obtain corresponding differential mode intracardiac signals and/or subtracting the common mode signal from the indifferent signal to obtain a corresponding differential mode indifferent signal.

Further according to one embodiment of the method for processing intracardiac signals, the method further comprises subtracting the differential mode indifferent signal from one or more of the differential mode intracardiac signals to generate respective unipolar intracardiac output signals.

Further according to one embodiment of the method for processing intracardiac signals, the method further comprises selectively applying a channel-specific filtering step to one or more of the differential mode intracardiac and indifferent signals prior to generating the intracardiac output signals;

Further according to one embodiment of the method for processing intracardiac signals, the average is the arithmetic mean of the intracardiac and indifferent signals.

According to one embodiment of the method for processing intracardiac signals, the average is the weighted arithmetic mean of the intracardiac and indifferent signals. In the special case that all weights are equal, the weighted arithmetic mean is equal to the arithmetic mean. By applying different weighting factors, the intracardiac and indifferent signals obtained from the respective channels of the differential amplifier stage contribute to the average at different weights. Such a configuration is advantageous in order to compensate to hardware related variations between the different channels. For example, such variations may be due to different amplification factors for the different channels.

According to some embodiments of the method for processing intracardiac signals, the number of intracardiac signals is 3, 4, 5, 6, 7, 8, 9, at least 10, up to or at least 20, up to or at least 50, up to or at least 100, or even more. Correspondingly, in some embodiments of the above-mentioned system for recording intracardiac signals, the number of intracardiac terminals is 3, 4, 5, 6, 7, 8, 9, at least 10, up to or at least 20, up to or at least 50, up to or at least 100, or even more.

Further according to one embodiment of the invention, a system for recording intracardiac signals according to any of the above-mentioned embodiments is adapted to performing the method for processing intracardiac signals according to any of the above-mentioned embodiments. At least a part of the system thus implements the method to obtain noise reduced intracardiac data, and in particular to obtain noise reduced intracardiac data for providing output signals with a reliable or at least reproducible morphology as discussed above.

BRIEF DESCRIPTION OF THE DRAWINGS

Preferred embodiments of the invention will be described in more detail in connection with the appended drawings, which show in FIG. 1 Schematic of a set-up including a system for recording intracardiac signals according to one embodiment of the invention, FIG. 2 composite plot of a first set of signals including intracardiac and indifferent signals, FIG. 3 composite plot of a second set of signals including intracardiac signals, FIG. 4 plot of the average of the signals of the second set, FIG. 5 composite plot of intracardiac data based on the intracardiac signals of the second set, FIG. 6 composite plot of a third set of signals including intracardiac signals, FIG. 7 plot of the average of the signals of the third set, FIG. 8 composite plot of intracardiac data based on the intracardiac signals of the third set, FIG. 9 plot of the average of the signals of the first set, FIG. 10 composite plot of differential mode intracardiac and indifferent signals obtained from the first set, FIG. 11 composite plot of intracardiac data with unipolar intracardiac output signals generated from the differential mode signals of the first set, FIG. 12 composite plot of differential mode intracardiac and indifferent signals of a fourth set of signals, shown on a larger scale, FIG. 13 composite plot of intracardiac data with unipolar intracardiac output signals generated from the differential mode signals of FIG. 12, FIG. 14 composite plot of the differential mode signals of FIG. 12 after selective filtering, and in FIG. 15 composite plot of intracardiac data with unipolar intracardiac output signals generated from the selectively filtered differential mode signals of FIG. 14.

DETAILED DESCRIPTION OF PREFERRED EMBODIMENTS

Figure 1:
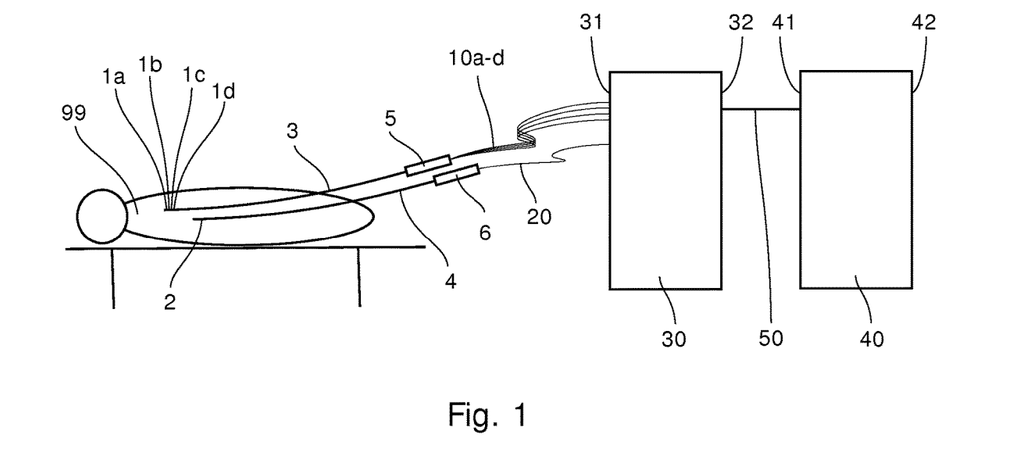

FIG. 1 shows schematically a set-up for recording intracardiac signals from an individual 99 using a system according to one embodiment of the invention. The system comprises a plurality of intracardiac terminals 10a-d that are connected to respective intracardiac electrodes 1a-d at the distal end of a multi-electrode catheter 3 via an interface 5 at the proximal end of the catheter 3. The system further comprises an indifferent terminal 20 that is connected to an intra-cardiovascular indifferent electrode 2 at the distal end of a catheter 4 via an interface 6 at the proximal end of the catheter 4. A typical set-up may include further apparatus, such as for 3D mapping catheter probes, for monitoring the individual, for stimulation of the heart, for applying defibrillation, and/or for performing ablation procedures. Such further apparatus has been omitted in FIG. 1 for reasons of clarity. The system further comprises a differential amplifier stage 30 and a processor device 40 communicating with each other via a link 50.

Prior to recording, the electrodes 1a-d have been placed in an intracardiac location in a known manner, e.g. in a minimally invasive procedure by means of a catheter 3 carrying the plurality of electrodes 1a-d. The intracardiac electrodes are located within the same heart chamber to be monitored and probe the intracardiac electrophysiological potentials at their respective intracardiac locations. Accordingly, the electrode 2 has been placed in an intra-cardiovascular location, e.g. in the inferior vena cava, by means of a catheter 4, and probes electrophysiological potentials that are considered indifferent with respect to the intracardiac electrophysiological potentials. The probed electrophysiological potentials from the electrodes 1a-d, 2 are transmitted to the interfaces 5, 6 at the proximal end of the catheters 3, 4 via respective leads. Advantageously, the intracardiac electrodes 1a-d and their respective leads are bundled in a single catheter 3, whereas the indifferent electrode 2 is placed on a separate catheter 4. However, different bundling combinations may be conceived, e.g. a set-up where the intracardiac electrodes 1a-d and the indifferent electrode 2 are grouped on one catheter, or a set-up comprising multiple catheters comprising multiple groups of intracardiac electrodes for simultaneously probing intracardiac potentials at respective locations. Furthermore, the number of four intracardiac electrodes shown in FIG. 1 is to be considered as an example and different numbers of intracardiac electrodes, such as 5, 6, 7, 8, 9, 10, 20, 50, 100, or even more may be conceived. The intracardiac potentials from the intracardiac electrodes 1a-d are collected at interface 5 by the respective intracardiac terminals 10a-d. Accordingly, the indifferent potential from the indifferent electrode 2 is collected at interface 6 by the indifferent terminal 20. While the indifferent potential provided at the interface 6 in the set-up shown in FIG. 1 is defined by a single electrode 2, it may also be conceived that the indifferent potential collected by the indifferent terminal 20 is defined as a combination of potentials probed by a plurality of electrodes.

The intracardiac and indifferent electrophysiological potentials collected by the terminals 10a-d, 20 are passed on the input side 31 of the differential amplifier stage 30 to respective amplifier channels where they are amplified with respect to a signal reference. The respective intracardiac and indifferent signals obtained from the amplifier stage 30 are passed from an output side 32, via link 50, to an input interface 41 of a processor device 40. The processor device 40 determines a common mode signal as an average of the intracardiac and indifferent signals received from the amplifier stage 30 and generates an output of intracardiac data at an output interface 42. The intracardiac data output is based at least on the intracardiac signals, wherein the intracardiac signals are referenced with respect to the common mode signal.

Preferably, the signal reference is common for all amplifier channels. In a particularly advantageous embodiment, the amplifier stage has an average reference amplifier configuration, wherein the average of all amplifier output signals is fed back to the input side of the amplifier stage and is used as the signal reference. Thereby a good first level suppression of mains interference as common mode noise is achieved already in the differential amplifier stage. Alternatively, the amplifier stage has a common reference amplifier configuration, wherein an indifferent potential may be used as common reference for all amplifier channels.

In the following, the advantageous processing of intracardiac signals by different embodiments of a method according to the present invention is described by way of example. Processing has been performed on different sets of signals that have been obtained on a pig 99 with a set-up corresponding to the one shown in FIG. 1, using a system 10, 20, 30, 40, 50 according to one embodiment of the system according to the invention.

Figure 2:
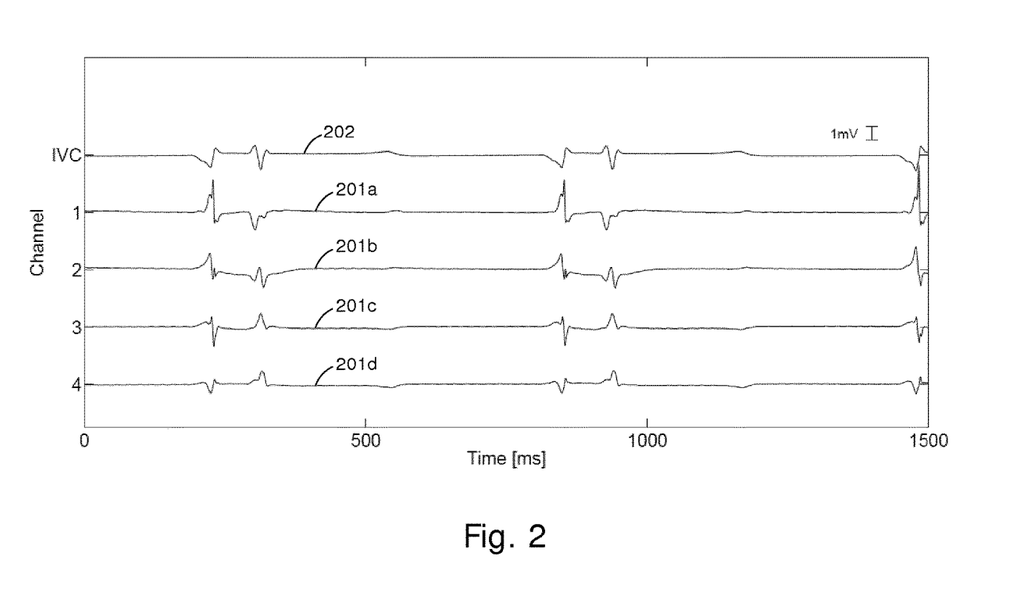
Figure 12:
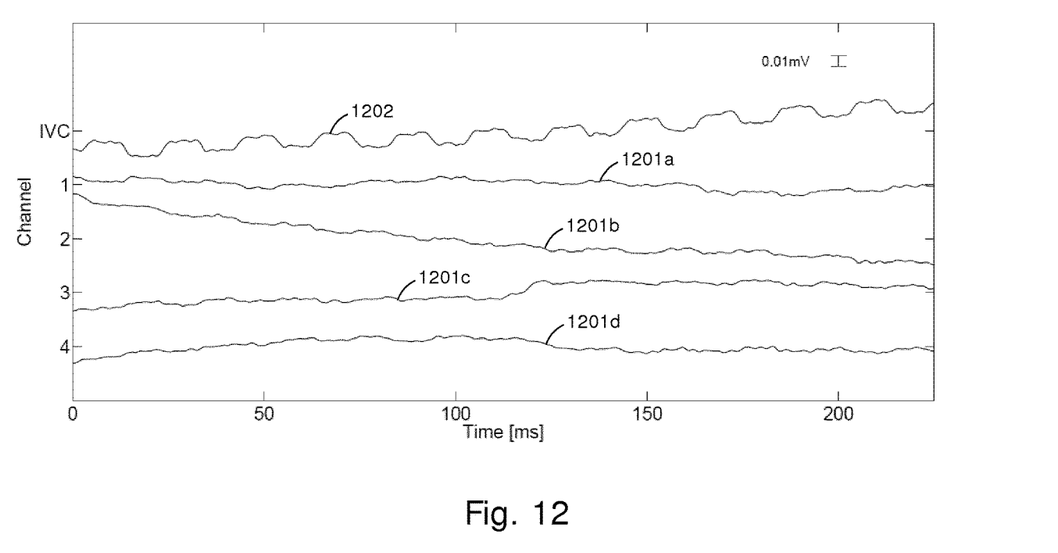
Figure 13:
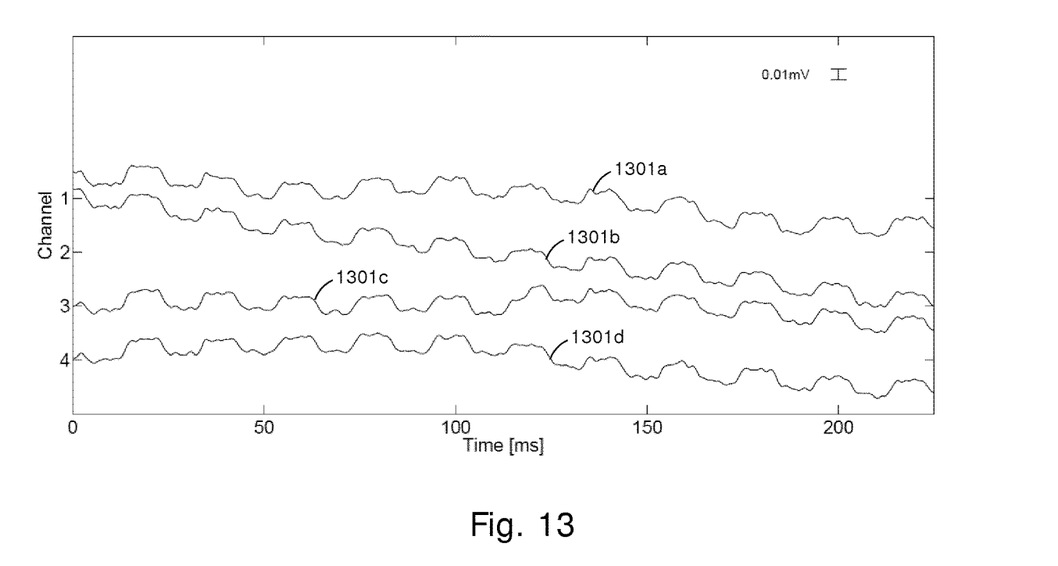
Figure 14:
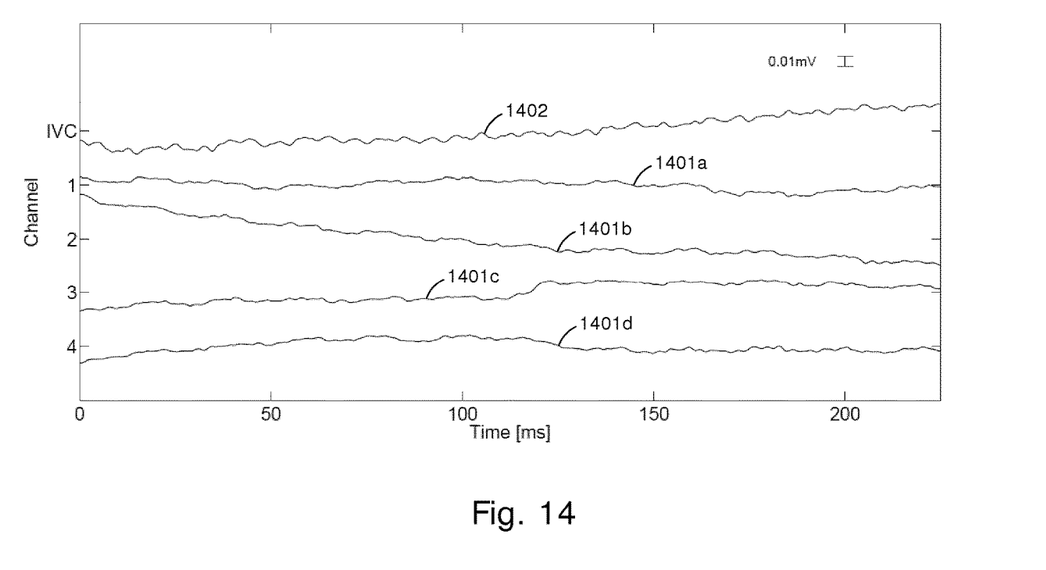

A first set of four intracardiac signals 201a-d (Channels 1-4) and one indifferent signal 202 (Channel IVC) is shown in the composite plot of FIG. 2, wherein all channels are shown on the same time scale and at the same vertical scale indicated by the vertical scale bar labelled 1 mV. The same time scale and vertical voltage scale also apply to the plots of FIGS. 3-11. The plots of FIGS. 12-14 are shown on a larger time scale and in particular on an about 80 times larger vertical voltage scale as indicated in each of the plots by the vertical scale bar labelled 0.01 mV.

The intracardiac and indifferent signals 201a-d, 202 shown in FIG. 2 have been obtained by amplifying intracardiac and indifferent potentials collected from the intracardiac and indifferent terminals 10a-d, 20 in an average reference amplifier configuration using the arithmetic mean of all five channels as the signal reference fed back to the input side 31 of the differential amplifier stage 30.

Figure 3:
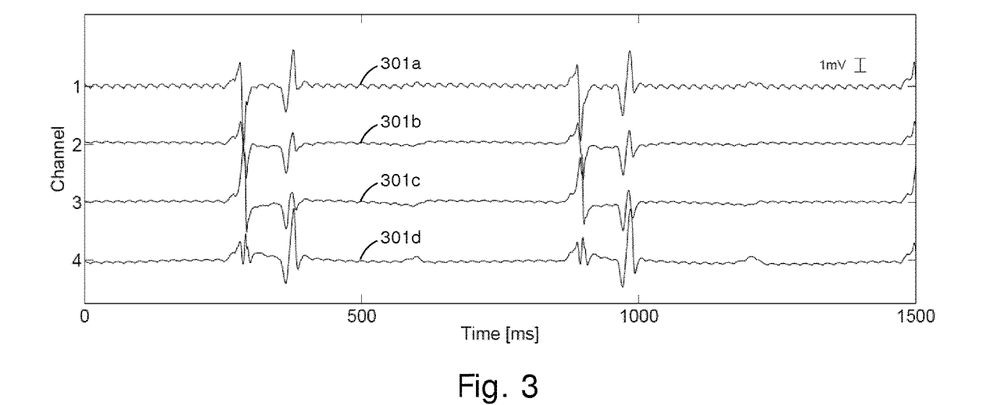
Figure 4:
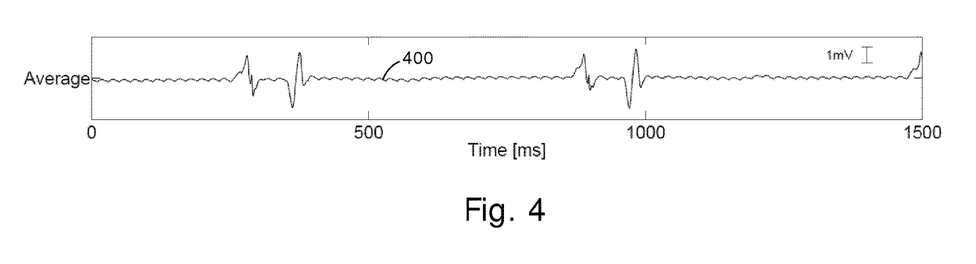
Figure 5:
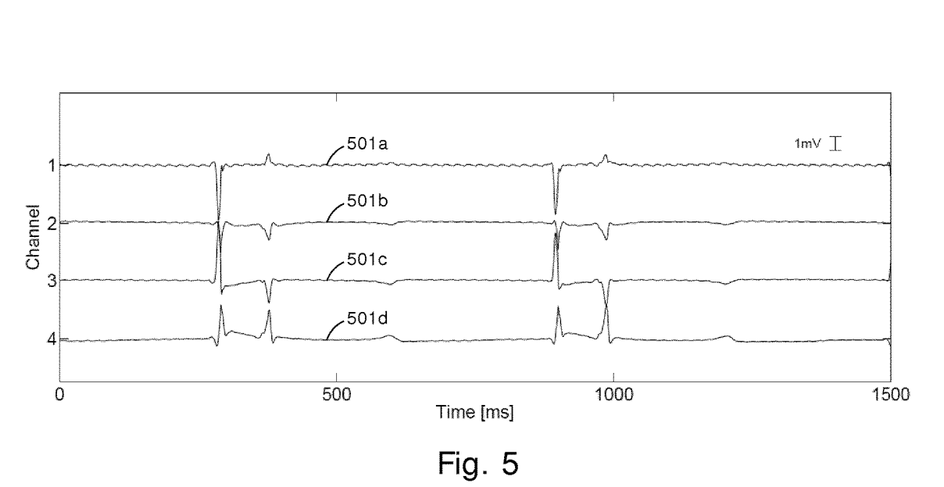

A second set of four intracardiac signals 301a-d (Channels 1-4) is shown in the composite plot of FIG. 3, wherein the intracardiac signals 301a-d have been obtained by amplifying intracardiac potentials collected from intracardiac terminals 10a-d in a common reference amplifier configuration using the potentials collected from the indifferent terminal 20 as a common signal reference for all intracardiac signals 301a-d. A prominent mains interference contribution is observed as a regular periodic ripple present in all intracardiac signals 301a-d. Note that no indifferent signal can be provided, since the indifferent terminal is used as a common signal reference. The intracardiac signals 301a-d of FIG. 3 are passed to the processor 40, and the common mode signal 400 of all four intracardiac signals 301a-d is determined as the arithmetic mean shown in FIG. 4. The common mode signal 400 of FIG. 4 is then subtracted from each of the intracardiac signals 301a-d of FIG. 3 to obtain the corresponding differential mode signals 501a-d shown in the composite plot of FIG. 5. The differential mode signals 501a-d may then be output as intracardiac data based on the intracardiac signals 301a-d of FIG. 3, wherein the intracardiac signals 301a-d are referenced with respect to the common mode signal 400. By referencing the intracardiac signals 301a-d to the common mode signal 400, the mains interference is clearly reduced, even though a remainder of the periodic ripple characteristic for mains interference is still evident.

Figure 6:
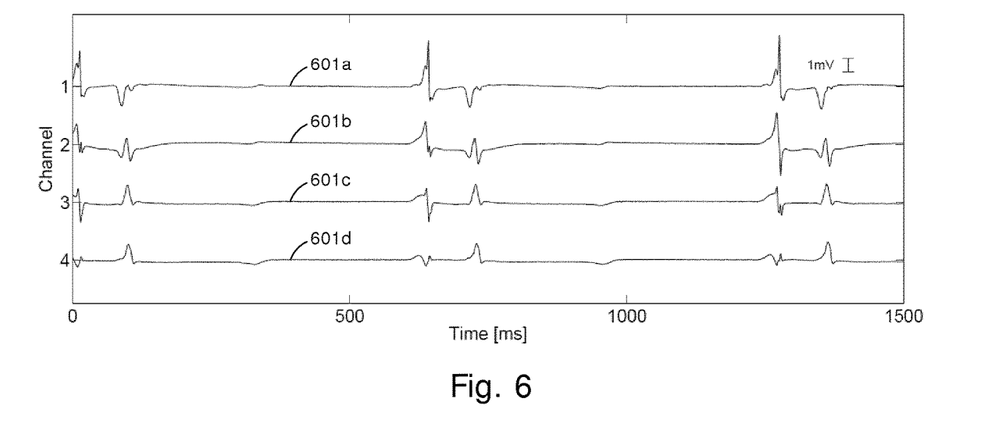
Figure 7:
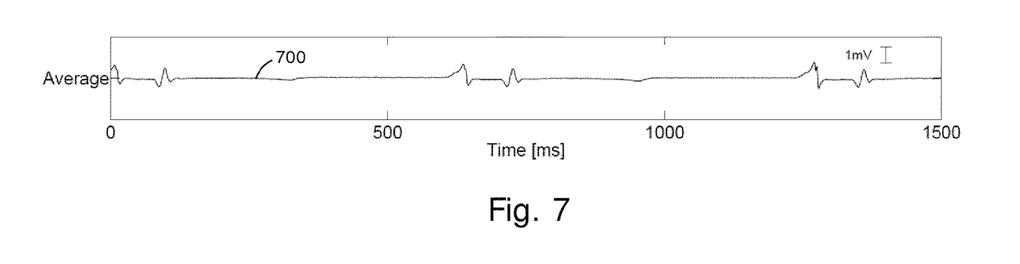
Figure 8:
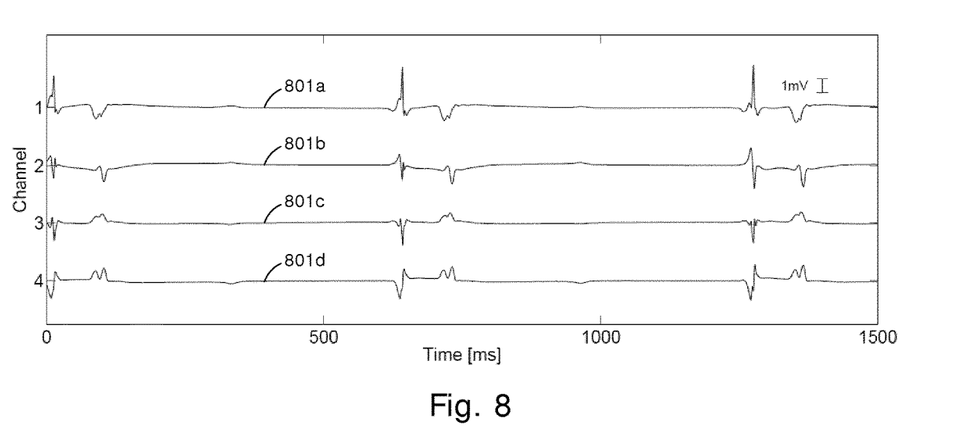

A third set of four intracardiac signals 601a-d (Channels 1-4) is shown in the composite plot of FIG. 6, wherein the intracardiac signals 601a-d have been obtained by amplifying intracardiac potentials collected from intracardiac terminals 10a-d in an average reference amplifier configuration feeding the arithmetic mean of the intracardiac signals 601a-d back to the input side 31 of the amplifier stage 30 as signal reference for all amplifier channels. The mains interference contribution is largely reduced as compared to the intracardiac signals obtained in the common reference amplifier configuration. As for the second set of signals, no indifferent signal is present in the third set. The intracardiac signals 601a-d of FIG. 6 are passed to the processor 40, and the common mode signal 700 of all four intracardiac signals 601a-d is determined as the arithmetic mean shown in FIG. 7. The common mode signal 700 of FIG. 7 is then subtracted from each of the intracardiac signals 601a-d of FIG. 6 to obtain the corresponding differential mode signals 801a-d shown in the composite plot of FIG. 8. The differential mode signals 801a-d may then be output as intracardiac data based on the intracardiac signals 601a-d of FIG. 6, wherein the intracardiac signals 601a-d are referenced with respect to the common mode signal 700. Also in this case, the mains interference is clearly reduced by referencing the intracardiac signals 601a-d to their common mode signal 700.

While subtracting the common mode signal from the intracardiac signals and also amplifying the intracardiac signals in an average amplifier configuration thus clearly achieves a significant improvement in terms of reducing the detrimental effects of mains interference on the intracardiac signals, this results in a distortion of the signals beyond recognition with respect to well-known unipolar signal shapes. The resulting deviant morphology can be seen e.g. in the above-mentioned differential mode intracardiac signals 501a-d and 801a-d and in a similar manner in the intracardiac signals 201a-d and 601a-d obtained in the average reference amplifier configuration as compared to the unipolar morphology of the more noisy intracardiac signal data 301a-d obtained in the common reference amplifier configuration. Furthermore, the morphology of intracardiac differential mode signals, such as signals 501a-d and 801a-d, as well as of intracardiac signals obtained from the average reference amplifier configuration, such as signals 201a-d and 601a-d, depends by definition on the actual intracardiac potentials probed and also on the actual number and location of the intracardiac electrodes 1a-d within the intracardiac region to be studied. The obtained intracardiac data may therefore be difficult to relate to a well-defined electrophysiological reference.

However, the deviant morphology may be repaired and a unipolar morphology may be restored by requiring that the set of signals in addition to the plurality of intracardiac signals collected from intracardiac terminals 10a-d also includes an indifferent signal from an indifferent terminal 20, and that the indifferent signal is included in the common mode signal to which the intracardiac signal is to be referenced. This is illustrated in the following by revisiting the first set of signals, which includes intracardiac signals 201a-d from intracardiac terminals 10a-d, and an indifferent signal 202 from an indifferent terminal 20.

Figure 9:
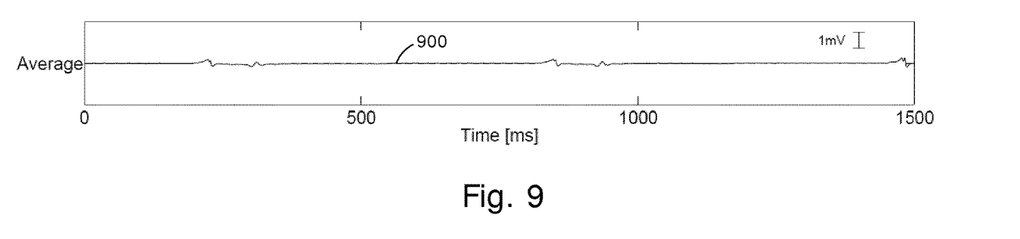
Figure 10:
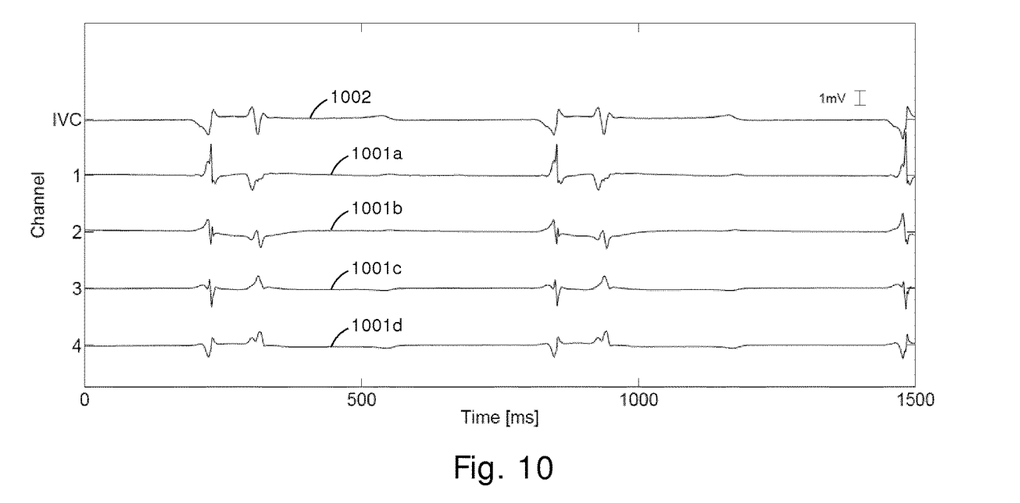
Figure 11:
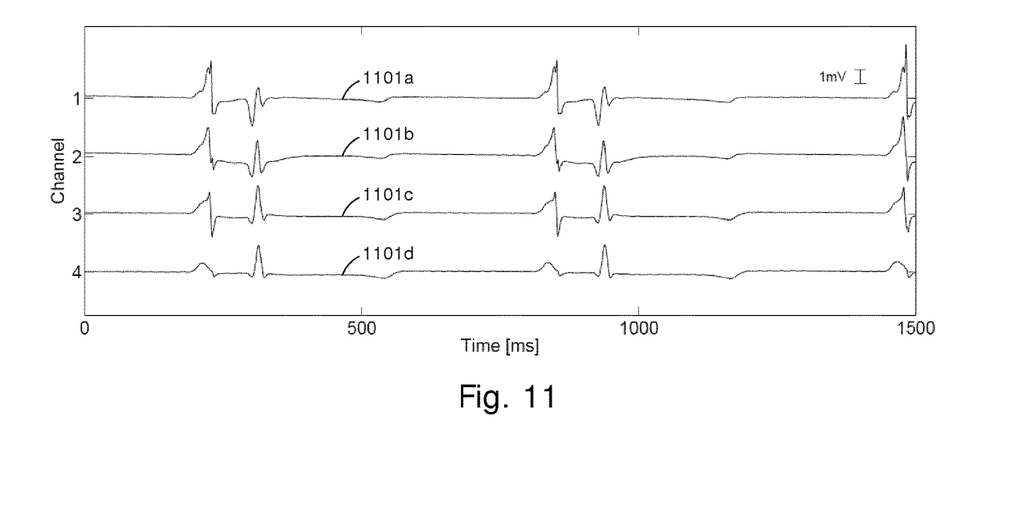

Just like in the previous embodiments for the second and third set of signals 301a-d and 601a-d, the signals provided by the amplifier stage 30 are passed to the processor 40. However, now the set of signals passed to the processor 40 includes both the intracardiac signals 201a-d and the indifferent signal 202. As mentioned above, the intracardiac and indifferent signals 201a-d, 202 are obtained in an average reference amplifier configuration leading to an efficient suppression of mains interference noise, but severely affects the morphology of the intracardiac signals. Analogue to the above mentioned embodiments, differential mode signals may be derived by determining the common mode signal 900 as the arithmetic mean of all five signals including the four intracardiac signals 201a-d and the indifferent signal 202. The common mode signal 900 is shown in FIG. 9. The common mode signal 900 of FIG. 9 is then subtracted from each of the intracardiac and indifferent signals 201a-d, 202 of FIG. 2 to obtain the corresponding differential mode signals 1001a-d, 1002 shown in the composite plot of FIG. 10. The differential mode intracardiac signals 1001a-d may again be output as intracardiac data for further use. The differential mode signals 1001a-d exhibit again very little mains interference. Yet again, the morphology of the differential mode signals 1001a-d is distorted as in the cases discussed above. However, since the set of signal includes a compatible indifferent signal, the morphology may be restored by either directly subtracting the indifferent signal 202 from the intracardiac signals 201a-d to generate respective unipolar intracardiac output signals (not shown), or by subtracting the differential mode indifferent signal 1002 from the differential mode intracardiac signals 1001a-d to generate respective unipolar intracardiac output signals 1101a-d.

The short-cut of directly subtracting the indifferent signal from the intracardiac signals is possible without compromising the noise suppression properties of the method, when the signals are referenced to a common mode signal already in the amplifier stage, e.g. in the above-mentioned average reference amplifier configuration, which is also applied for the first set of signals 201a-d, 202. Including the steps of deriving the differential mode signals first before performing the subtraction is also possible in this case where the intracardiac signals are referenced to the common mode signal already in the amplifier stage. However, the additional step of deriving the differential mode signals first is particularly advantageous, when efficient common mode suppression could not be applied or simply has not been applied to the signals in the amplifier stage.

Figure 15:
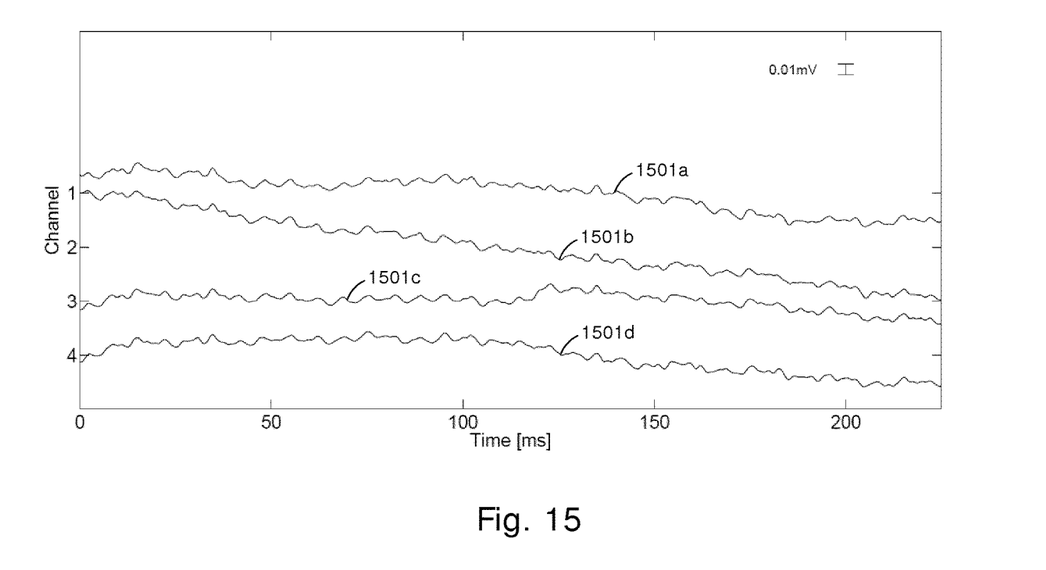

A further improvement of the noise reduction may be achieved by selectively applying a channel-specific filtering step to one or more of the intracardiac and indifferent signals, or differential mode intracardiac and indifferent signals, prior to generating the intracardiac output signals. This is described by way of example in the following for a fourth set of signals including a plurality of intracardiac signals and an indifferent signal. FIG. 12 shows the respective differential mode intracardiac and indifferent signals 1201a-d, 1202 obtained by subtracting the common mode signal from the intracardiac and indifferent signals. On the large scale of this plot, the differential mode indifferent signal 1202 clearly exhibits a remaining mains interference signal as evident from the periodic ripple, whereas a corresponding noise component is absent from the differential mode intracardiac signals 1201a-d. FIG. 13 shows the respective unipolar intracardiac output signals 1301a-d generated by subtracting the differential mode indifferent signal 1202 from the differential mode intracardiac signals 1201a-d. The noisy differential mode indifferent signal 1202 clearly contaminates the unipolar intracardiac output signals 1301a-d. FIG. 14 shows a composite plot of differential mode intracardiac and indifferent signals 1401a-d corresponding to those of FIG. 12 after a selective filtering step has been applied. In fact, the differential mode intracardiac signals 1401a-d are identical to the differential mode intracardiac signals 1201a-d. Only the differential mode indifferent signal 1202 has selectively been subjected to a filtering step, thereby removing the remaining periodic ripple and obtaining the filtered differential mode indifferent signal 1402. As a result, unipolar intracardiac output signals 1501a-d as shown in FIG. 15 may be obtained with a significantly reduced noise contamination from the filtered differential mode indifferent signal 1402.

The invention claimed is:

1. System for recording intracardiac signals and for providing stimulation pulses and/or ablation energy at intracardiac locations, the system comprising:
   a plurality of intracardiac terminals adapted to collecting intracardiac electrophysiological potentials from a plurality of passive intracardiac electrodes at respective intracardiac locations in an individual;
   an indifferent terminal adapted to collecting indifferent electrophysiological potentials from one or more indifferent electrodes in or on the individual;
   a differential amplifier stage adapted to receiving and amplifying the electrophysiological potentials collected from the intracardiac and indifferent terminals with respect to a signal reference to obtain respective intracardiac and indifferent signals; and
   a processor device 40 adapted to determining a common mode signal as an average of the intracardiac and indifferent signals and adapted to providing an output of intracardiac data based at least on the intracardiac signals, wherein the intracardiac signals are referenced with respect to the common mode signal.

2. System according to claim 1, wherein the differential amplifier stage is an average reference amplifier, wherein the average of the intracardiac and indifferent signals is fed back as a signal reference to the input side of the differential amplifier stage so as to reference the intracardiac signals and the indifferent signal to the common mode signal.

3. System according to claim 1, wherein the processor device is further adapted to determining respective differential mode intracardiac signals by subtracting the common mode signal from the intracardiac signals so as to reference the intracardiac signals to the common mode signal.

4. System according to claim 3, wherein the processor device is further adapted to determining a differential mode indifferent signal by subtracting the common mode signal from the indifferent signal.

5. System according to claim 1, wherein the intracardiac data comprises
an ensemble of the differential mode intracardiac signals and/or the differential mode indifferent signal;
an ensemble of unipolar intracardiac signals obtained by subtracting the indifferent signal from the intracardiac signals; or
an ensemble of unipolar intracardiac signals obtained by subtracting the differential mode indifferent signal from the differential mode intracardiac signals; or
an ensemble of bipolar intracardiac signals obtained by subtracting a second one of the intracardiac signals from a first one of the intracardiac signals; or
an ensemble of bipolar intracardiac signals obtained by subtracting a second one of the differential mode intracardiac signals from a first one of the differential mode intracardiac signals.

6. System according to claim 1, wherein the indifferent terminal is adapted to collecting indifferent electrophysiological potentials from one or more indifferent electrodes probing an intra-cardiovascular location in the individual.

7. Method for processing intracardiac signals, the method comprising:
receiving multiple sequences of electrophysiological potentials collected from a plurality of passive intracardiac electrodes via corresponding intracardiac terminals and from at least one indifferent electrode via a corresponding indifferent terminal;
amplifying the electrophysiological potentials in a differential amplifier stage with respect to a signal reference to obtain respective intracardiac and indifferent signals;
determining a common mode signal as an average of the intracardiac and indifferent signals; and
providing an output of intracardiac data based at least on the intracardiac signals, wherein the intracardiac signals are referenced with respect to the common mode signal.

8. Method according to claim 7, further comprising feeding the average of the intra-cardiac and indifferent signals back to the input side of the amplifier stage in an average reference amplifier configuration so as to reference the intracardiac signals and the indifferent signal with respect to the common mode signal.

9. Method according to claim 8, further comprising subtracting the indifferent signal from one or more of the intracardiac signals to generate respective unipolar intracardiac output signals.

10. Method according to claim 9, further comprising selectively applying a channel-specific filtering step to one or more of the intracardiac and indifferent signals prior to generating the intracardiac output signals.

11. Method according to claim 7, further comprising subtracting the common mode signal from one or more of the intracardiac signals to obtain corresponding differential mode intracardiac signals and/or subtracting the common mode signal from the indifferent signal to obtain a corresponding differential mode indifferent signal.

12. Method according to claim 11, further comprising subtracting the differential mode indifferent signal from one or more of the differential mode intra-cardiac signals to generate respective unipolar intracardiac output signals.

13. Method according to claim 12, further comprising selectively applying a channel-specific filtering step to one or more of the differential mode intracardiac and in-different signals prior to generating the intracardiac output signals.

14. Method according to claim 7, wherein the average is the arithmetic mean of the intracardiac and indifferent signals.

15. System according to claim 2, wherein the processor device is further adapted to determining respective differential mode intracardiac signals by subtracting the common mode signal from the intracardiac signals so as to reference the intracardiac signals to the common mode signal.

16. System according to claim 2, wherein the indifferent terminal is adapted to collecting indifferent electrophysiological potentials from one or more indifferent electrodes probing an intra-cardiovascular location in the individual.

17. System according to claim 3, wherein the indifferent terminal is adapted to collecting indifferent electrophysiological potentials from one or more indifferent electrodes probing an intra-cardiovascular location in the individual.

18. System according to claim 4, wherein the indifferent terminal is adapted to collecting indifferent electrophysiological potentials from one or more indifferent electrodes probing an intra-cardiovascular location in the individual.

19. System according to claim 5, wherein the indifferent terminal is adapted to collecting indifferent electrophysiological potentials from one or more indifferent electrodes probing an intra-cardiovascular location in the individual.

20. System according to claim 1, wherein the intracardiac data comprises
an ensemble of the differential mode intracardiac signals and/or the differential mode indifferent signal;
an ensemble of unipolar intracardiac signals obtained by subtracting the indifferent signal from the intracardiac signals;
an ensemble of unipolar intracardiac signals obtained by subtracting the differential mode indifferent signal from the differential mode intracardiac signals;
an ensemble of bipolar intracardiac signals obtained by subtracting a second one of the intracardiac signals from a first one of the intracardiac signals; and
an ensemble of bipolar intracardiac signals obtained by subtracting a second one of the differential mode intracardiac signals from a first one of the differential mode intracardiac signals.

* * * * *